(12) United States Patent
Peterson et al.

(10) Patent No.: US 10,368,843 B2
(45) Date of Patent: Aug. 6, 2019

(54) ULTRASONIC SHEAR WAVE IMAGING WITH FOCUSED SCANLINE BEAMFORMING

(75) Inventors: Roy Beck Peterson, Seattle, WA (US); Yan Shi, White Plains, NY (US); Hua Xie, Ossining, NY (US); Jean-Luc Robert, White Plains, NY (US); Vijay Shamdasani, Seattle, WA (US); Robert Randall Entrekin, Kirkland, WA (US); Anna Teresa Ferandez, Falls Church, VA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 576 days.

(21) Appl. No.: 13/511,307

(22) PCT Filed: Nov. 15, 2010

(86) PCT No.: PCT/IB2010/055179
§ 371 (c)(1),
(2), (4) Date: Oct. 24, 2012

(87) PCT Pub. No.: WO2011/064688
PCT Pub. Date: Jun. 3, 2011

(65) Prior Publication Data
US 2013/0131511 A1    May 23, 2013

Related U.S. Application Data

(60) Provisional application No. 61/264,277, filed on Nov. 25, 2009.

(51) Int. Cl.
*A61B 5/00* (2006.01)
*A61B 8/00* (2006.01)
(Continued)

(52) U.S. Cl.
CPC ............ *A61B 8/485* (2013.01); *A61B 5/0048* (2013.01); *A61B 8/08* (2013.01); *A61B 8/14* (2013.01);
(Continued)

(58) Field of Classification Search
USPC .................................. 73/596, 609, 618, 627
See application file for complete search history.

(56) References Cited

U.S. PATENT DOCUMENTS 4,644,795 A    2/1987  Augustine
5,318,033 A    6/1994  Savord
(Continued)

FOREIGN PATENT DOCUMENTS

JP    8191834 A       7/1996
JP    2004313485 A    11/2004
(Continued)

OTHER PUBLICATIONS

Hoyt et al. Real-Time Shear Velocity Imaging Using Sonoelastographic Techniques. Ultrasound In Medicine & Biology. 33(7):1086-1097. Jul. 2007.*
(Continued)

*Primary Examiner* — Amelie R Gillman
(74) *Attorney, Agent, or Firm* — Sherry Womack Austin

(57) ABSTRACT

An ultrasonic diagnostic imaging system produces an image of shear wave velocities by transmitting push pulses to generate shear waves. A plurality of tracking lines are transmitted and echoes received by a focusing beamformer adjacent to the location of the push pulses. The tracking lines are sampled in a time-interleaved manner. The echo data acquired along each tracking line is processed to determine the time of peak tissue displacement caused by the shear waves at points along the tracking line, and the times of peaks at adjacent tracking lines compared to compute a local
(Continued)

shear wave velocity. The resultant map of shear wave velocity values is color-coded and displayed over an anatomical image of the region of interest.

19 Claims, 5 Drawing Sheets

(51) Int. Cl.
  *A61B 8/08* (2006.01)
  *A61B 8/14* (2006.01)
  *G01S 7/52* (2006.01)
  *G01S 15/89* (2006.01)

(52) U.S. Cl.
  CPC ............ *A61B 8/463* (2013.01); *A61B 8/5223* (2013.01); *G01S 7/52022* (2013.01); *G01S 7/52042* (2013.01); *G01S 7/52071* (2013.01); *G01S 7/52095* (2013.01); *A61B 8/085* (2013.01); *G01S 15/8984* (2013.01)

(56) References Cited

U.S. PATENT DOCUMENTS

| | | | |
|---|---|---|---|
| 5,345,426 A | 9/1994 | Lipschutz | |
| 5,469,851 A | 11/1995 | Lipschutz | |
| 5,606,971 A | 3/1997 | Sarvazyan | |
| 5,810,731 A | 9/1998 | Sarvazyan et al. | |
| 6,014,473 A * | 1/2000 | Hossack et al. | 382/294 |
| 6,494,838 B2 | 12/2002 | Cooley | |
| 6,558,324 B1 * | 5/2003 | Von Behren | A61B 8/08 600/437 |
| 6,695,783 B2 * | 2/2004 | Henderson et al. | 600/443 |
| 7,252,004 B2 | 8/2007 | Fink | |
| 7,374,538 B2 * | 5/2008 | Nightingale et al. | 600/443 |
| 8,197,408 B2 | 6/2012 | Fan et al. | |
| 2002/0010398 A1 * | 1/2002 | Bonnefous | 600/442 |
| 2008/0249408 A1 * | 10/2008 | Palmeri | A61B 8/08 600/438 |
| 2010/0138163 A1 * | 6/2010 | Gallippi | A61B 8/485 702/19 |
| 2010/0222678 A1 * | 9/2010 | Bercoff | A61B 8/08 600/442 |

FOREIGN PATENT DOCUMENTS

| | | |
|---|---|---|
| JP | 2009201989 | 9/2009 |
| WO | 2008139245 A1 | 11/2008 |

OTHER PUBLICATIONS

Bouchard et al. "Image quality, tissue heating, and frame rate trade-offs in acoustic radiation force impulse imaging." IEEE Trans. on Ultrasonics, Ferroelectrics, and Frequency Control. Jan. 2009; 56(1):63-76.*

Fontanilla et al. Ultrasound in Med. & Biol., vol. 40, No. 3, pp. 470-477, 2014.*

Manapurama et al. Laser Physics vol. 22, No. 9, 2012.*

M. Tanter et al: "Quantitative Assessment of Breast Lesion Viscoelasticity: Initial Clinical Results Using Supersonic Shear Imaging", Ultrasound in Medicine and Biology, New York, NY, US, vol. 34, No. 9, Sep. 1, 2008 (Sep. 1, 2008), pp. 1373-1386.

J. Bercoff et al: "Supersonic Shear Imaging: A New Technique for Soft Tissue Elasticity Mapping", IEEE Transactions on Ultrasonics, Ferroelectrics and Frequency Control, IEEE, US, vol. 51, No. 4, Apr. 1, 2004 (Apr. 1, 2004), pp. 396-409.

"Using Level Set Based Inversion of Arrival Times to Recover Shear Wave Speed in Trasient Elastography and Supersonic Imaging" Mclaughlin et al, Institute of Physics Publishing Inverse Problems 22 (2006) p. 707-725.

* cited by examiner

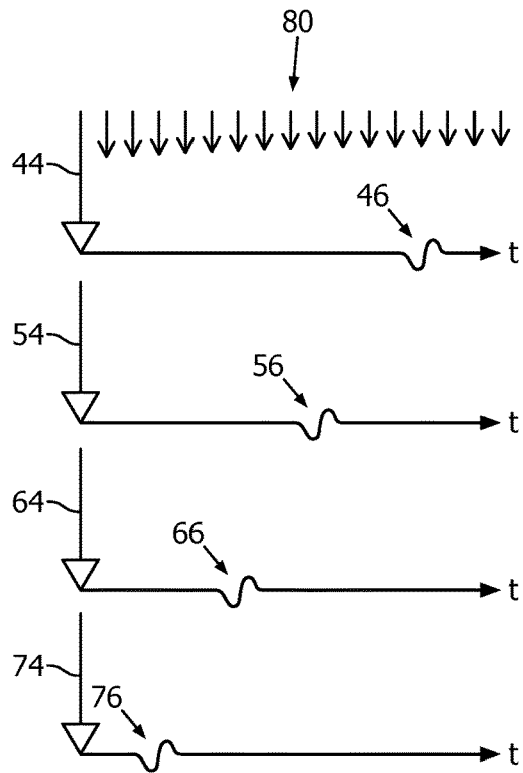
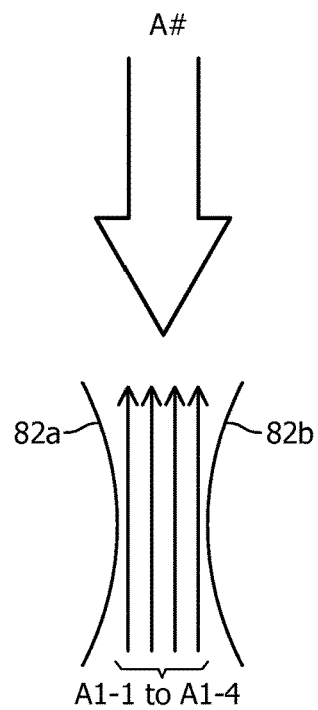
FIG. 3    FIG. 4
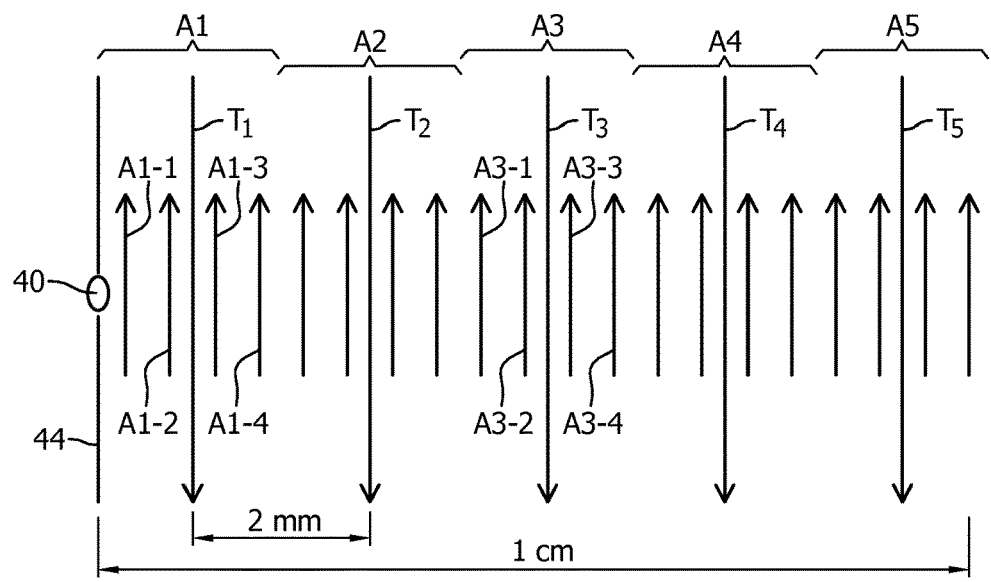
FIG. 5

ULTRASONIC SHEAR WAVE IMAGING WITH FOCUSED SCANLINE BEAMFORMING

This invention relates to medical diagnostic ultrasound systems and, in particular, to ultrasound systems which perform measurements of tissue stiffness or elasticity using shear waves.

One of the long-sought goals of diagnostic imaging is precise tissue characterization. A clinician would like to obtain a diagnostic region of an organ of the body and have the imaging system identify the characteristics of the tissue in the image. Ideally, the clinician would like the imaging system to identify a lesion as malignant or benign. While fully obtaining this objective remains yet to be accomplished, diagnostic imaging can nonetheless give the clinician clues as to the makeup of tissue. One technique in this area is elastography, which measures the elasticity or stiffness of tissues in the body. For example, breast tumors or masses with high stiffness might be malignant, whereas softer and more compliant masses are likely to be benign. Since the stiffness of a mass is known to correlate with malignancy or benignity, elastography provides the clinician with another piece of evidence to aid in diagnosis and determination of a treatment regimen.

Elastography as initially contemplated assessed tissue in the body when subjected to compressive pressure. When an ultrasound probe is pressed firmly against the body, underlying soft tissue will compress to a greater degree than underlying hard tissue. But elastography can be very operator-dependent, with results being influenced by where and how much pressure is being applied to the body. It would be desirable to be able to assess elasticity by a method which is not so operator-dependent.

An alternate approach to elasticity measurement is shear wave measurement. When a point on the body is compressed, then released, the underlying tissue is compressed downward, then rebounds back up when the compressive force is released. But since the tissue under the compressive force is continuously joined to surrounding tissue, the uncompressed tissue lateral of the force vector will respond to the up-and-down movement of the compressed tissue. A rippling effect in this lateral direction, referred to as a shear wave, is the response in the surrounding tissue to the downward compressive force. Furthermore, it has been determined that the force needed to push the tissue downward can be produced by the radiation pressure from an ultrasound pulse, and ultrasound reception can be used to sense and measure the tissue motion induced by the shear waves. Shear wave velocity is determined by local tissue mechanical properties. The shear wave will travel at one velocity through soft tissue, and at another, higher velocity through hard tissue. By measuring the velocity of the shear wave at a point in the body, information is obtained as to characteristics of the tissue such as its shear elasticity modulus, Young's modulus, and dynamic shear viscosity. The laterally propagating shear wave travels slowly, usually a few meters per second or less, making the shear wave susceptible to detection, although it attenuates rapidly over a few centimeters or less. See, for example, U.S. Pat. No. 5,606,971 (Sarvazyan) and U.S. Pat. No. 5,810,731 (Sarvazyan et al.) Since the same "push pulse" can be repeated for each measurement, the shear wave technique lends itself to objective quantification of tissue characteristics with ultrasound. Furthermore, the shear wave velocity is independent of the push pulse intensity, making the measurement less dependent upon the user.

In conventional pulse-echo ultrasound, an ultrasound pulse is transmitted out from the probe and echoes reflected back from tissue encountered by the pulse are received directly. However, since the shear wave travels laterally, it cannot be directly received absent a laterally situated acoustic window for a receiver. See, for example, FIG. 2 of the Sarvazyan et al. patent, which suggests receiving shear waves at a different side of the tissue from the transmitter when measuring shear waves in the breast. But such a technique requires separate transmitters and receivers, and differently situated acoustic windows are not always available. Thus, researchers have looked for indirect ways to measure the shear wave. A common way to do this is to acquire successive sets of image data of the tissue, then process the data to detect the propagation of the shear wave through the tissues as manifested in the resultant tissue motion caused by the shear wave. See the Sarvazyan and Sarvazyan et al. patents for a discussion of this approach. The acquired echo data, when ultrasound is used as opposed to MRI, can be processed by the known ultrasonic techniques for detecting motion, including Doppler and correlation of sequential echo data.

But it requires time to acquire a series of data sets and, as previously mentioned, the shear waves rapidly attenuate in the tissue, which poses a problem of resolving the motion in sufficient detail to measure the propagation velocity of the small amplitude shear wave, which typically causes a tissue displacement of less than 30 micrometers. A solution to this problem has been advanced by Fink et al. in U.S. Pat. No. 7,252,004, who propose to observe the propagation of the shear wave by rapidly acquiring images from unfocused plane waves, each insonifying a large expanse of tissue and repeated at a rate of at least 500 repetitions per second, and preferably in the range of 1000 to 5000 repetitions per second. Rather than acquire an image by transmitting and receiving individual lines of data across the image field, which entails a full transmit-receive cycle for each line, Fink et al. insonify the entire region of interest (ROI) with a single unfocused wave, then acquire echoes resulting from the wave transmission through the tissue during a subsequent reception period. (Sarvazyan takes an analogous approach by tying all of the elements of his transducer in parallel during reception.) Since each interrogation of the ROI only requires a single wave transmission, data sets can be successively acquired at the high rate that Fink et al. desire. While the unfocused wave lacks both the signal-to-noise performance and the focal resolution of individual image lines, Fink et al. intend to offset this deficiency with their high rate of data acquisition. It would be desirable, however, to be able to observe and measure the propagation velocity of a shear wave with precision and good signal-to-noise performance and to do so with conventional ultrasound systems.

In accordance with the principles of the present invention, a diagnostic ultrasonic imaging system and method are described which enables a user to acquire highly resolved image data sufficient to measure the velocity of a shear wave propagating through tissue. One or more push pulses are transmitted into tissue with an ultrasound probe to ultrasonically compress the tissue in the vectorial direction of the push pulses. Immediately thereafter, focused tracking pulses are transmitted and received by the probe in the vicinity of the push pulse vector which generates the shear wave. Each tracking pulse vector is repetitively sampled in a time-interleaved manner so that motion produced by a shear wave can be detected when it occurs at each tracking pulse vector location, preferably by correlating the echo data from successive interrogations of the vector. As the shear wave moves laterally away from the push pulse vector, the positioning of the tracking pulses can also be moved laterally to follow the propagation of the shear wave. The data from the repetitively sampled tracking pulse vectors is processed to find the times at which the shear wave causes a peak displacement at each point of the tracking pulse vector, preferably by cross-correlation, curve-fitting or interpolating successive displacement measurements. Analysis of the times at which points on adjacent sampling vectors experience peak displacement produces a measurement corresponding to the velocity of the shear wave at particular vector locations, with velocity variations indicating tissues of different stiffness or elasticity. Since the shear waves attenuate so rapidly, it is generally not possible to acquire shear wave data from an entire image field with a single push pulse vector. Thus, the process is repeated at another location in the tissue to acquire shear wave velocity measurements at another region of the tissue. The process is repeated until shear wave data has been acquired over the desired image field. The velocity information is preferably presented as a two- or three-dimensional image of the tissue, color-coded by the shear wave velocity data at points in the image.

FIG. 3 spatially illustrates a sequence of pulse pulses along a push pulse vector, the resultant shear wavefront, and a series of tracking pulse vectors.

FIG. 4 illustrates the transmission and reception of 4× multiline for the production of four adjacent multiline tracking pulse vectors.

FIG. 5 illustrates four laterally adjacent groups of 4× multiline tracking pulse vectors.

Figure 6:
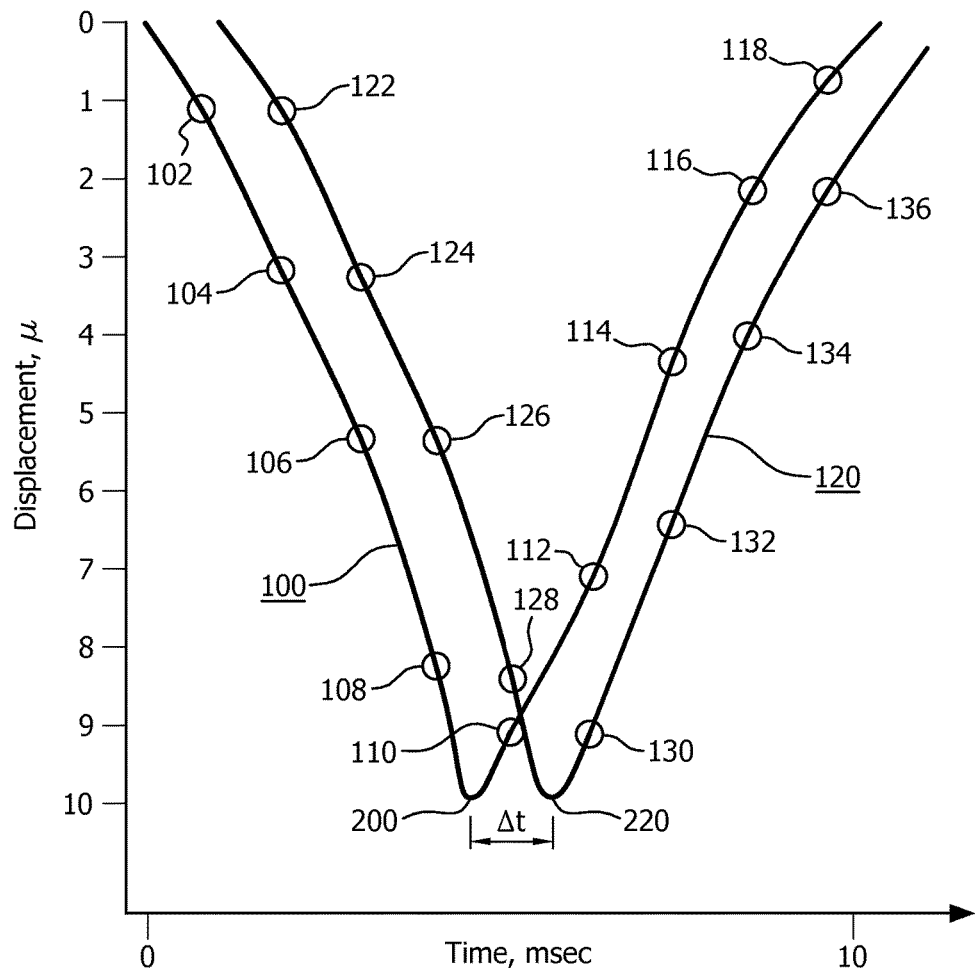

FIG. 6 illustrates shear wave displacement curves at two locations as it progresses through tissue.

Figure 7A:
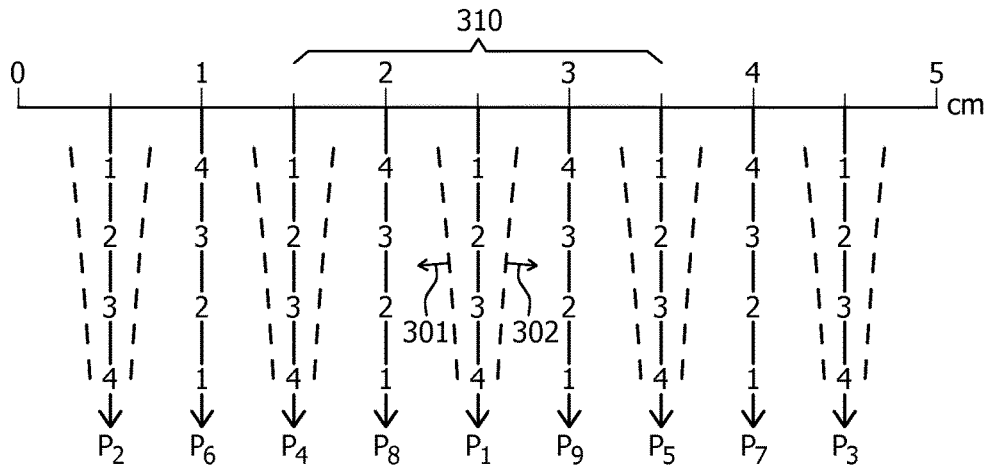
Figure 7B:
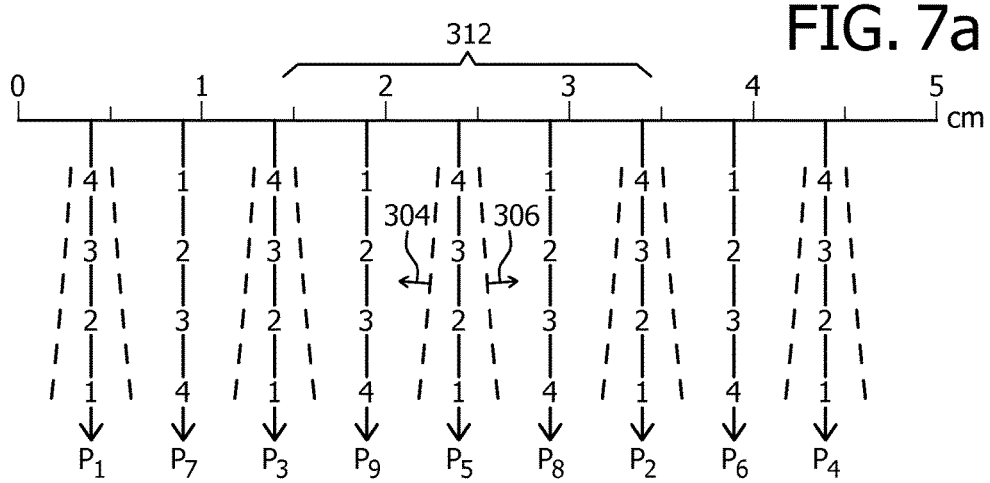
Figure 7C:
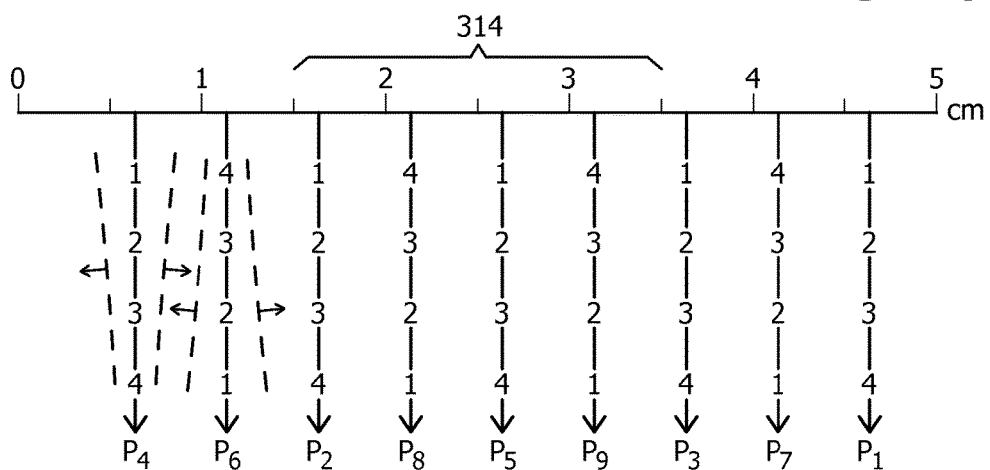

FIGS. 7a-7c illustrate a spatially time-interleaved sequence of push pulse vectors distributed laterally over an image field.

Figure 1:
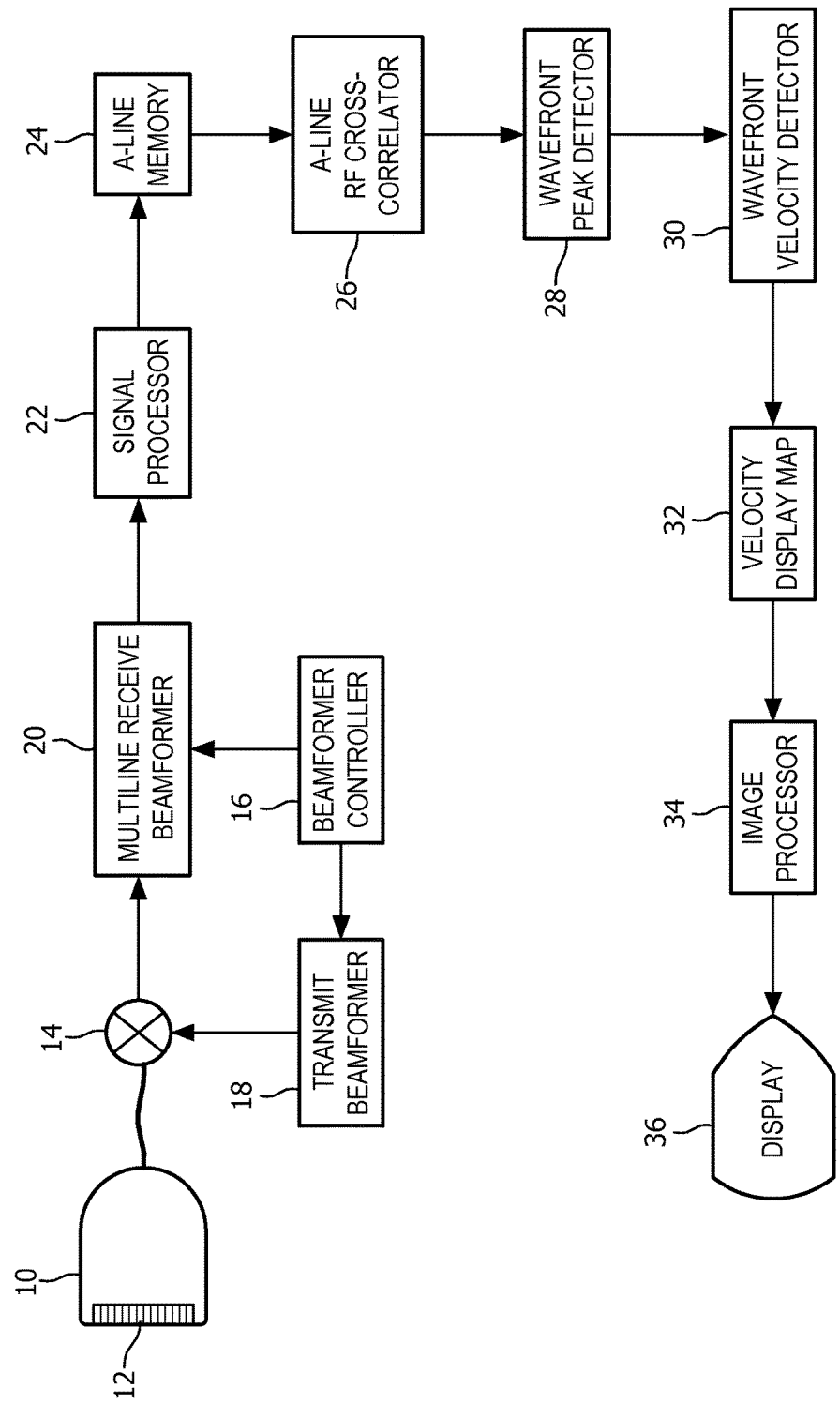
FIG. 1 illustrates in block diagram form an ultrasonic diagnostic imaging system constructed in accordance with the principles of the present invention.

Referring first to FIG. 1, an ultrasound system constructed in accordance with the principles of the present invention for the measurement of shear waves is shown in block diagram form. An ultrasound probe 10 has a transducer array 12 of transducer elements for transmitting and receiving ultrasound signals. The array can be a one dimensional or a two dimensional array of transducer elements. Either type of array can scan a 2D plane and the two dimensional array can be used to scan a volumetric region in front of the array. The array elements are coupled to a transmit beamformer 18 and a multiline receive beamformer 20 by a transmit/receive (T/R) switch 14. Coordination of transmission and reception by the beamformers is controlled by a beamformer controller 16. The multiline receive beamformer produces multiple, spatially distinct receive lines (A-lines) of echo signals during a single transmit-receive interval. The echo signals are processed by filtering, noise reduction, and the like by a signal processor 22, then stored in an A-line memory 24. Temporally distinct A-line samples relating to the same spatial vector location are associated with each other in an ensemble of echoes relating to a common point in the image field. The r.f. echo signals of successive A-line sampling of the same spatial vector are cross-correlated by an A-line r.f. cross-correlator 26 to produce a sequence of samples of tissue displacement for each sampling point on the vector. Alternatively, the A-lines of a spatial vector can be Doppler processed to detect shear wave motion along the vector, or other phase-sensitive techniques can be employed. A wavefront peak detector 28 is responsive to detection of the shear wave displacement along the A-line vector to detect the peak of the shear wave displacement at each sampling point on the A-line. In a preferred embodiment this is done by curve-fitting, although cross-correlation and other interpolative techniques can also be employed if desired. The time at which the peak of the shear wave displacement occurs is noted in relation to the times of the same event at other A-line locations, all to a common time reference, and this information is coupled to a wavefront velocity detector 30 which differentially calculates the shear wave velocity from the peak displacement times on adjacent A-lines. This velocity information is coupled into a velocity display map 32 which indicates the velocity of the shear wave at spatially different points in a 2D or 3D image field. The velocity display map is coupled to an image processor 34 which processes the velocity map, preferably overlaying the anatomical ultrasound image of the tissue, for display on an image display 36.

Figures 2A, 2B, 2C, 2D:
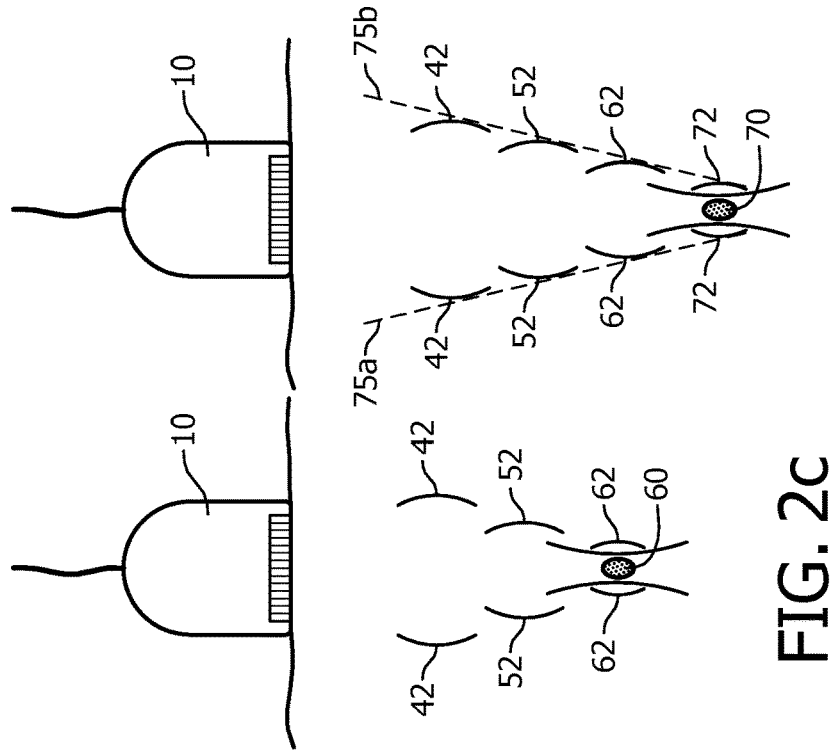
FIGS. 2a-2d illustrate the transmission of a sequence of push pulses to different depths to produce a shear wavefront.

FIGS. 2a-2d illustrate the transmission of a sequence of focused high MI push pulses (e.g., MI of 1.9 or less so as to be within FDA diagnostic limits) along a single vector direction to produce a shear wavefront. Pulses of high MI and long durations are used so that sufficient energy is transmitted to displace the tissue downward along the transmit vector and cause the development of a shear wave. In FIG. 2a the probe 10 at the skin surface 11 transmits a first push pulse 40 into the tissue with a beam profile 41a, 41b to a given focal depth indicated by the shaded area 40. This push pulse will displace the tissue at the focus downward, resulting in a shear wavefront 42 emanating outward from the displaced tissue.

FIG. 2b illustrates a second push pulse 50 transmitted by the probe 10 along the same vector and focused at the deeper depth of the shaded area 50. This second push pulse 50 displaces the tissue at the focal depth, causing a shear wavefront 52 to emanate outward from the displaced tissue. Thus, shear wavefronts 42 and 52 are both propagating laterally through the tissue, with the initial wavefront 42 preceding the second.

FIGS. 2c and 2d illustrate the transmission by probe 10 of two more push pulses 60 and 70, each at a successively greater depth and each producing an outward emanating shear wavefront 62 and 72. It is seen in FIG. 2d that the composite wavefront of the four push pulses, indicated by the dashed lines 75a and 75b, extends for an appreciable depth in the tissue, from the shallow depth of the first push pulse 40 to the deepest depth of the fourth push pulse 70. This enables shear wave measurement over an appreciable depth of tissue. In an implementation described below, this technique is used to detect shear wave propagation over a depth of 6 cm., a suitable depth for breast imaging and diagnosis.

It will be appreciated that a greater or lesser number of push pulses can be transmitted along the push pulse vector, including a single push pulse. Multiple push pulses can be transmitted in any order, with the order determining the shape and direction of the composite shear wavefront. For example, if the push pulses of FIGS. 2a-2d were transmitted in sequence from the deepest (70) to the shallowest (40), the composite shear wavefront of FIG. 2d would have the inverse tilt to that shown in FIG. 2d. In a preferred embodiment each push pulse is a long pulse of 50 to 200 microseconds in duration. A typical duration is 100 microseconds, for instance. The ultrasound produced during the 100 microsecond pulse duration are compressional wave pulses and can have a frequency of 7 or 8 MHz, for example. The push pulses are well focused, preferably at an f number of 1 or 2. In an implementation of the four push pulse sequence shown in FIG. 2a-2d, a push pulse is transmitted every 2.5 milliseconds, giving the push pulses a 400 Hz transmission frequency. In another implementation, all four push pulses are transmitted in one sequence to launch the full shear wavefront before the tracking A-lines begin.

FIG. 3 is another illustration of the use of four push pulses to create a composite shear wavefront. The four push pulses are transmitted along vectors 44, 54, 64 and 74 which are seen to be aligned along a single vectorial direction in FIG. 3. When the shallowest push pulse of vector 44 is transmitted first followed by successively deeper push pulses, the shear wavefronts of the respective push pulses will have propagated as indicated by waves 46, 56, 66, and 76 by a time shortly after the last push pulse (vector 74) has been transmitted. As the shear waves 46, 56, 66, and 76 travel outward from the push pulse vector, they are interrogated by tracking pulses 80 shown in spatial progression along the top of the drawing. Tracking pulses can occur between as well as after push pulses.

In accordance with the principles of the present invention, the velocity of the laterally traveling shear wave is detected by sensing the tissue displacement caused by the shear wave as it proceeds through the tissue. This is done with time-interleaved sampling pulses transmitted adjacent to the push pulse vector as shown in FIG. 5. In this example the push pulse(s) 40 is transmitted along push pulse vector 40 to cause a laterally traveling shear wave. A-line vectors adjacent to the push pulse vector 40 are sampled by sampling pulses T1, T2, T3, T4, and T5 transmitted along each vector in a time-interleaved sequence. For example, the first vector location A1 is sampled by a first pulse T1, then the second vector location A2 by the next pulse T2, then A3, A4, and A5. Then vector location A1 is sampled again, and the sequence repeats. Since the sampling is time-interleaved, each of the five vector locations is sampled once in every five sampling pulses in this example. In this example every vector location is pulsed fifty-five times for a total tracking time of 27.5 msec. Each pulse results in echoes returning from along the vector which are sampled by a high speed A/D converter. Thus, for every sampled point along each vector there is an ensemble of 55 samples, with each sample taken at one-fifth the pulse rate of the T1-T5 sampling pulse sequence. The sampling rate will be chosen in consideration of the frequency content of the shear wave displacement being detected so as to satisfy the Nyquist criterion for sampling. Since the purpose of the sampling is to sense and track the displacement effect of the shear wave as it progresses through the tissue, the vector locations may be located closer together for slowly moving shear waves and further apart for more rapidly moving shear waves. Other sequences of time-interleaving the vector sampling may also be employed. For example, odd-numbered vectors could be sampled in sequence, followed by sampling of the even-numbered vectors. As another example, vector locations A1-A3 could be sampled in a time-interleaved manner, then vector locations A2-A4, then vector locations A3-A5 to track the shear wave displacement as it progresses. Other sequences may also be employed based upon the exigencies of the situation. The ensembles of time-interleaved samples at each point along each sampling vector are then processed to find the time of peak tissue displacement at each point of each vector as described in detail below.

In accordance with a further aspect of the present invention, multiline transmission and reception is employed so that a single tracking pulse can simultaneously sample a plurality of adjacent, tightly spaced, A-line locations. Referring to FIG. 4, a preferred technique for multiline transmission and reception is shown. In FIG. 4 a single A-line tracking pulse with a beam profile 82a, 82b which insonifies multiple receive line locations is transmitted as indicated by the wide arrow A#. Preferably the tracking pulse is a so-called "fat pulse" as described in U.S. Pat. No. 4,644,795 (Augustine), for example. In this example four receive line locations A1-1, A1-2, A1-3 and A1-4 are insonified. Echoes from the four receive lines (4× multiline) are received in response to the single transmit pulse and are appropriately delayed and summed to produce coherent echo signals along each of the receive lines. Beamformer capable of producing such simultaneous multilines are described, for instance, in U.S. Pat. No. 5,318,033 (Savord), U.S. Pat. No. 5,345,426 (Lipschutz), U.S. Pat. No. 5,469,851 (Lipschutz), and U.S. Pat. No. 6,695,783 (Henderson et al.) These multiline beamformers are typically used to decrease the acquisition time and thereby increase the frame rate of live ultrasound images, which is particularly useful when imaging the beating heart and blood flow in real time echocardiography. They are also useful in 3D ultrasound imaging so that real time frame rates of display can be attained. See, in this regard, U.S. Pat. No. 6,494,838 (Cooley et al.) In an implementation of the present invention, the benefit of multiline acquisition is two-fold: it enables a closely-spaced sampling line density and rapid acquisition of a short duration shear wave which only travels a short distance through tissue before being dissipated by attenuation. While higher order multiline may be employed which acquires samples along a greater number of A-lines at the same time and thus a higher sampling rate, this will require a broader transmit beam (A#) to simultaneously insonify the greater number of receive lines. The broader transmit beam will consequently diminish the signal-to-noise performance of the higher order implementation.

FIG. 5 illustrates the use of 4× multiline reception for transmission and reception along each sampling vector A1-A5. A first tracking pulse $T_1$ is transmitted close to the push pulse vector 44, insonifying four receive line locations A11-1 to A1-4 and four multiline A-lines are received in response from the adjacent lateral region A1. When the four multilines are centered with respect to the transmitted tracking pulse, echoes from two A-lines are received on each side of the center of the tracking pulse beam center, shown by A1-1 and A1-2 to the left of center and A1-3 and A1-4 to the right of center. In a preferred embodiment the A-lines are spaced 0.5 mm apart from each other. Shear waves generally move at a speed of 1-10 meters per second, and consequently tracking pulses are repetitively transmitted down regions A1-A5 in a time-interleaved manner and A-line samples received from the A-line locations during the time intervals between push pulses (when there are such intervals), and for 20 msec after the last push pulse, after which the shear wave has propagated out of the one centimeter A1-A5 sampling window. Since shear waves can have frequency components in the range of about 100 Hz to about 1000 Hz, sampling theory dictates that each A-line should have a sampling rate of 2 kHz. This results in a set (ensemble) of fifty-five A-line samplings of each sampling point on each multiline A-line.

In the example of FIG. 5, five tracking pulses, $T_1$-$T_5$, are transmitted over successive sampling windows A1-A5 adjacent to the push pulse vector 44 to sample the shear wave displacement effect as the wave propagates. A typical sampling pulse is a short pulse, usually only one or two cycles, at a frequency suitable for penetrating the depth being studied, such as 7-8 MHz. Each tracking pulse is offset by 2 mm from its adjacent neighbors, resulting in twenty A-lines spaced 0.5 mm apart with 4× multiline over a total distance of one centimeter. There are various ways the interrogate the sampling windows. One is to just sample region A1 until the shear wave is detected, then to begin sampling in region A2, then A3, and so on. Another is to time interleave the sampling in the regions as described above, sampling with tracking pulses $T_1$-$T_5$ in succession, then repeating the sequence. With the latter approach five sampling windows with twenty tracking A-line positions can track the shear wave effect simultaneously. After the shear wave has passed through the closest A1 sampling window, then the adjacent windows, sampling of that window can be terminated and the sampling time can be devoted to the remaining sampling windows through which the shear wave is still propagating. Sampling continues until the shear wave has propagated out of the one cm. sampling region, by which time the shear wave has usually attenuated below a detectable level. Shear waves on average have a relaxation time of 10 msec.

It is necessary that the sampling times of the tracking A-line positions be related to a common time base when the tracking pulses are time-interleaved so that the results can be used to make a continuous measurement of time, and hence velocity, across the one cm. sampling region. For example, since the sampling pulses for sampling window A2 do not occur until 50 microseconds following the corresponding sampling pulses for window A1, a 50 microsecond time offset exists between the sampling times of the two adjacent windows. This time difference must be taken into account when comparing the peak times of displacement in the respective windows, and must be accounted for in an accumulated manner across the full one centimeter sampling window. Referencing the sampling times of each sampling vector to a common time reference can resolve the problem of the offset sampling times.

It will be appreciated that the shear wave emanates outward radially from the vector where the push pulse has displaced the tissue. This means that a shear wave can be tracked on either side of the push pulse vector in a 2D image plane through the tissue. In the example of FIG. 5 the shear wave is shown being tracked to the right of the push pulse vector 44, although it could also be tracked as it propagates to the left of the vector. The shear wave could also be tracked on both sides of the push pulse vector at the same time by time-interleaving tracking pulses on both sides of the push pulse vector, but without being able to sample a full centimeter region on both sides of the push pulse without sacrificing the sampling line density, line sampling frequency (PRF), shear wave tracking distance, or some combination thereof.

Since a diagnostic region-of-interest (ROI) is generally greater than one centimeter in width, the procedure of FIG. 5 is repeated with push pulses transmitted at different lateral locations across the image field. An image field is thereby interrogated in one cm. wide regions, and the results of the regions are displayed adjacent to each other to present an image of the full ROI. In a preferred implementation a Philips Healthcare L12-5 probe is used, which has a 5 cm. aperture. A four cm. wide image field is interrogated in four adjacent or overlapping one cm. regions, which are then displayed side-by-side or wholly or partially overlaid on the display.

FIG. 6 illustrates a sequence of displacement values for two laterally adjacent points on two adjacent A-lines such as A1-3 and A1-4 in FIG. 5. Curve 100 represents the displacement over time caused by passage of a shear wave through a point on A-line A1-3, and curve 120 the displacement at an adjacent point of A-line A1-4. Points 102-118 of tissue displacement values are calculated from local cross correlations of r.f. data (e.g., 10-30 r.f. samples in depth) acquired around a sampling point depth on A1-3 over time to yield the local displacement values over time at the depth point. The points 102-118 of displacement values detected at successive times (y-axis), when plotted as a function of time, are joined to form the first displacement curve 100. At a point on second A-line A-1-4 spaced to the right of the point on the first A-line, the succession 122-136 of displacement values produced by local cross correlation can be joined to form a second displacement curve 120. Since the shear wave is traveling from left to right in this example, the second curve 120 for the right-most A-line is shifted to the right (in time) of the first displacement curve 100. A precise time reference of the passage of the wavefront from one point to the next is measured by the detected peak or inflection point of each displacement curve, indicated at 200 and 220 in this example. Various techniques can be used to find the curve peak. In a preferred embodiment the displacement values of each curve are processed by fitting curves to the values to form complete displacement curves 100, 120 and the curve peaks. Another technique is to interpolate additional points between the detected points to find the peak. Yet another technique is to determine the slopes of the curve on either side of the peak and determine the peak from the intersection of slope lines. Still another approach is cross-correlation of the curve data. When the peaks of the shear wave displacement at successive A-line positions are found by the waveform peak detector 28, their times of occurrence in relation to the detection of the points on the curves are noted. The difference of these times, $\Delta t$, taking into consideration sampling time offsets, and the spacing between the A-lines (e.g., 0.5 mm) can then be used by the wavefront velocity detector 30 to determine the velocity of the shear wave as it traveled between the two A-line locations. After the entire ROI has been interrogated in this manner and displacement curves and times of peak occurrence determined for each sample point on each A-line vector, the velocity of shear wave travel can be calculated from point to point across the entire region of interest. This two dimensional matrix of velocity values is color-coded or otherwise coded in a display variation to form a velocity display map. The velocity display map is shown on the display 36, preferably overlaid and in spatial alignment with a B mode image of the region of interest.

In the above example shear waves were detected and measured as they traveled horizontally through a region of interest. However, many lesions are rounded or otherwise appear as two-dimensional objects in a 2D image. To accurately locate the border of a circular lesion it would be ideally desirable to direct shear waves at the lesion from a full 360° radius of directions around the lesion. Directing shear waves along one set of directional paths and compounding the results with measurements taken of shear waves traversing other directional paths through the ROI can produce more precise and reliable images of lesions and their borders. One way to do this is to dither the push pulse vectors and sequences across the image field as illustrated by FIGS. 7*a*-7*c*. These figures show a series of push pulses in relation to a fixed 5 cm. wide region of interest. The push pulses are differently sequenced, spatially interleaved, and spatially dithered to interrogate the region of interest with differently directed shear waves. In addition, the temporal and spatial interleaving reduces the build-up of energy at any particular point in the image field which could exceed desired thermal limits in the body. The scanning begins in FIG. 7a with a push pulse vector $P_1$ in the center of the image field (2.5 cm. point) of four push pulses, 1-4, which are sequenced from a shallow to a deeper depth in the image field. As explained above, these four push pulses will produce a composite shear wavefront which is tilted to propagate in a slightly downward direction as indicated by arrows 301 and 302. The next push pulse vector, $P_2$, is transmitted on the left side of the image field (0.5 cm. point), well removed to the left of the previous push pulse. Since successive push pulse vectors are not adjacent to each other but are widely spatially offset, the thermal effects of the two push pulse vectors are separated so they cannot accumulate at any one point. In a similar fashion the third push pulse vector $P_3$ is located at the far right of the image field (4.5 cm. point), the next push pulse vector $P_4$ is located to the left of the field center (1.5 cm. point), and so on. Nine push pulse vectors are transmitted in this spatially separated fashion in FIG. 7a.

It is also seen that the sequence of the pulses of the vectors changes. Vectors $P_1$-$P_5$ use a sequence of push pulses beginning at the shallowest depth and ending at the deepest depth (1-4), while vectors $P_6$-$P_9$ use a sequence from deep to shallow (4-1). This results in an alternation in push pulse sequence from vector to vector across the image field.

The pulse sequence of FIG. 7b follows that of FIG. 7a and begins with push pulse vector $P_1$ at the left of the image field (0.5 cm. point). This push pulse vector is well offset from the preceding vector, which was $P_9$, to the right of the center of the image field in FIG. 7a. Vector $P_1$ in FIG. 7b is also seen to have the reverse pulse sequence from its spatially corresponding vector $P_2$ in FIG. 7a. The sequence of vector $P_2$ in FIG. 7b is from deep to shallow, whereas the sequence for vector $P_2$ in FIG. 7a was shallow to deep. This causes the shear waves from vector $P_1$ in FIG. 7b to travel slightly upward (see arrows 304 and 306), whereas the shear waves from vector $P_2$ in FIG. 7a traveled slightly downward (see arrows 301 and 302). In addition, vector $P_1$ in FIG. 7b is shifted slightly to the left of the 0.5 cm. point of the image field, whereas vector $P_2$ in FIG. 7a (and all the other vectors of FIG. 7a) is aligned with the 0.5 cm. point of the field. This shifting is done across the image field, which can be seen by comparing the alignment of the five vectors of bracket 310, which are aligned with the centimeter markers, with the five vectors of bracket 312, which are all seen to be shifted to the left of the centimeter markers. The combination of these differences further lessens the build-up of energy at a particular point in the image, and is also seen to direct shear waves along differing propagation paths from FIG. 7a to FIG. 7b. As before, successively transmitted push pulse vectors are widely separated, and the sequencing of the push pulses alternates from vector to vector across the image field. If desired, the focal points of the push pulses can also be varied between vectors.

This sequence of transmit variation is seen to continue in FIG. 7c. In this sequence of nine push pulse vectors it is seen that the push pulse vectors are shifted to the right of the centimeter markers, which can be seen by comparing the vectors under bracket 314 with those under brackets 310 and 312. By the use of such combinations of pulse sequencing and spatial shifting and separation, heating effects can be minimized and velocity measurements from differently directed shear waves can be compounded by averaging or the like to produce more reliable elasticity quantification.

What is claimed is:

1. An ultrasonic diagnostic imaging system for shear wave analysis comprising:
   an ultrasound probe comprising a two-dimensional array;
   a beamformer configured to control the following:
      transmit, from the ultrasound probe, push pulses along a plurality of push pulse vectors to generate a corresponding plurality of shear wave fronts each having a respective velocity, wherein the plurality of push pulse vectors are spatially interleaved in a lateral direction and the push pulses are differently sequenced in a depth direction along different ones of the plurality of push pulse vectors;
      transmit, from the ultrasound probe, tracking pulses along laterally separated tracking lines in a region adjacent to the plurality of push pulse vectors, wherein the tracking pulses are transmitted along the laterally separated tracking lines in a time-interleaved sequence such that the laterally separated tracking lines may be sampled a plurality of times after the push pulses are transmitted; and
      receive, from the ultrasound probe, echo signals from points along the laterally separated tracking lines to sample the laterally separated tracking lines the plurality of times after the push pulses are transmitted; and
   a processor configured to:
      store tracking line echo data generated from the received echo signals as the corresponding plurality of shear wave fronts pass through the laterally separated tracking lines;
      in response to the tracking line echo data, detect motion due to the shear wave fronts passing through the tracking lines, wherein detecting motion comprises successively sampling the tracking line echo data;
      measure the respective velocities of the corresponding plurality of shear wave fronts passing through the laterally separated tracking lines; and
      display results of measuring the respective velocities of the corresponding plurality of shear wave fronts.

2. The ultrasonic diagnostic imaging system of claim 1, wherein the detecting motion comprises detecting tissue displacement caused by the corresponding plurality of shear wave fronts.

3. The ultrasonic diagnostic imaging system of claim 2, wherein the detecting motion comprises cross-correlating the tracking line echo data to detect motion of wavefront peaks of the corresponding plurality of shear wave fronts.

4. The ultrasonic diagnostic imaging system of claim 3, wherein measuring the respective velocities comprises comparing times of occurrence of two displacement peaks in the corresponding plurality of shear wave fronts.

5. The ultrasonic diagnostic imaging system of claim 1, wherein the displaying comprises displaying a two dimensional image of the respective velocities of the corresponding plurality of shear wave fronts.

6. The ultrasonic diagnostic imaging system of claim 5, wherein the respective velocities of the corresponding plurality of shear wave fronts are color-coded and overlaid on an anatomical image.

7. The ultrasonic diagnostic imaging system of claim 1, wherein the beamformer comprises a multiline beamformer.

8. The ultrasonic diagnostic imaging system of claim 1, wherein the detecting motion comprises detecting a time of peak tissue displacement at the points along the laterally separated tracking lines.

9. The ultrasonic diagnostic imaging system of claim 8, wherein the detecting motion comprises detecting a plurality of displacement values by local cross correlation of the tracking line echo.

10. The ultrasonic diagnostic imaging system of claim 9, wherein the detecting motion comprises detecting a time of peak tissue displacement by curve-fitting to the plurality of displacement values.

11. The ultrasonic diagnostic imaging system of claim 9, wherein the detecting motion comprises detecting a time of peak tissue displacement by interpolating the plurality of displacement values.

12. The ultrasonic diagnostic imaging system of claim 7, wherein the multiline beamformer is adapted to detect the echo signals from the plurality of laterally spaced tracking lines in response to a single tracking pulse of the tracking pulses.

13. The ultrasonic imaging system of claim 1, wherein the push pulse vectors are spatially dithered in the lateral direction.

14. The ultrasonic imaging system of claim 1, wherein the plurality of push pulse vectors are spatially interleaved such that a push pulse vector of the plurality of push pulse vectors is offset such that the thermal effects of the plurality of push pulse vectors are separated, such that thermal effects cannot accumulate at any one point.

15. The ultrasonic imaging system of claim 1,
wherein the push pulses are differently sequenced in the depth direction along different ones of the plurality of push pulse vectors such that the push pulses along a first push pulse vector of the plurality of push pulse vectors are sequenced beginning at a first depth and ending at a second depth and the push pulses along a second push pulse vector of the plurality of push pulse vectors are sequenced beginning at the second depth and ending at the first depth,
wherein the second depth is deeper than the first depth.

16. A method for operating an ultrasonic diagnostic imaging system to measure shear waves comprising:
transmitting, using an ultrasound probe comprising a two-dimensional array, at least one transmission of push pulses along each of a plurality of push pulse vectors to generate a corresponding plurality of shear wave fronts each having a respective velocity, wherein the plurality of push pulse vectors are spatially interleaved in a lateral direction and push pulses of the at least one transmission of push pulses along each of the plurality of push pulse vectors are differently sequenced in a depth direction along different ones of the plurality of push pulse vectors;
transmitting, using the ultrasound probe, a plurality of focused tracking pulses along a plurality of laterally separated tracking lines adjacent to the plurality of push pulse vectors, wherein transmitting the plurality of focused tracking pulses comprises transmitting the plurality of focused tracking pulses along each of the plurality of laterally separated tracking lines in a time-interleaved manner such that the plurality of laterally separated tracking lines may be sampled a plurality of times after the push pulses have been transmitted;
receiving, using the ultrasound probe, focused echo signals in response to the transmission of the plurality of focused tracking pulses to sample the plurality of laterally separated tracking lines the plurality of times after the at least one transmission of push pulses has been transmitted;
processing, using an ultrasound system, the echo signals to determine shear wave velocity values at a plurality of points in two or three dimensions in a region of interest; and
displaying on a display a two or three dimensional image of the respective velocities of the corresponding plurality of shear wave fronts at the plurality of points.

17. The method of claim 16, wherein receiving focused echo signals further comprises receiving the focused echo signals from along the laterally spaced tracking lines in response to each transmission of the plurality of tracking pulses.

18. The method of claim 16, wherein processing further comprises processing the echo signals to determine tissue motion resulting from the corresponding plurality of shear wave fronts.

19. The method of claim 18, wherein processing further comprises processing the echo signals to determine tissue displacement along the plurality of points in two or three dimensions in the region of interest.

* * * * *